United States Patent [19]
Schauenstein et al.

[11] Patent Number: 5,837,474
[45] Date of Patent: Nov. 17, 1998

[54] IMMUNOLOGICAL METHOD FOR THE DETECTION OF MALIGNANT TUMORS AND KIT FOR PERFORMING THE METHOD

[76] Inventors: Erwin Schauenstein, Am Eisernen Tor 2, A-8010; Konrad Schauenstein, Carnerigasse 20, A-8010, both of Graz; Franz Dachs, Spattendorf 10, A-4210, Gallneukirchen, all of Austria

[21] Appl. No.: 295,720

[22] PCT Filed: Feb. 25, 1993

[86] PCT No.: PCT/AT93/00032

§ 371 Date: Jan. 30, 1995

§ 102(e) Date: Jan. 30, 1995

[87] PCT Pub. No.: WO93/17343

PCT Pub. Date: Sep. 2, 1993

[30] Foreign Application Priority Data

Feb. 27, 1992 [AU] Australia ................................. 368/92

[51] Int. Cl.$^6$ ................ G01N 33/574; G01N 33/53; G01N 33/48; A01N 1/02
[52] U.S. Cl. ............... 435/7.23; 435/2; 435/975; 436/63; 436/64; 436/514; 436/515; 436/813; 436/826
[58] Field of Search ............... 435/7.23, 2, 975; 436/514, 515, 541, 813, 826, 64

[56] References Cited

U.S. PATENT DOCUMENTS 4,219,539  8/1980  Deutsch .
4,757,002  7/1988  Joo ............................................. 435/7
5,227,405  7/1993  Fridovich et al. ....................... 514/612

OTHER PUBLICATIONS

Fluorescence Changes in Human Gamma–Globulin Induced . . . , D.G. Wickens et al., 1983, Elsevier Biomedical Press, pp. 607–616.

Schauenstein et al. "Labile disulfide bonds and free thiol groups in human IgG II. Characteristic changes in malignant diseases corresponding to shifts of IgG1 and IgG2 subclasses" Int. Archs. Allergy appl. Immuno. 80, pp. 180–184, 1986.

Smola et al "SS, a measure of reactive sulfur groups of immunoglobulin G, is a sensitive tumor marker discriminating different stages of breast cancer" Cancer vol. 68, pp. 1026–1030, 1991.

Khanna et al "Serum immunoglobulins in squamous cell carcinoma of the oral cavity" J. of Surg. Oncology, vol. 20, pp. 46–48, 1982.

European Patent Office, Database WPI, Section Ch, Week 7239, Derwent Publications Ltd, London, GB; Class A03, AN 72–62480T & JP–47 037530 (Yamada).

*Primary Examiner*—Toni R. Scheiner
*Assistant Examiner*—Yvonne Eyler
*Attorney, Agent, or Firm*—Herbert L. Lerner; Laurence A. Greenberg; Werner H. Stemer

[57] ABSTRACT

A method of detecting malignant tumors and determining their mass includes withdrawing fresh blood and/or serum samples from the patient. The blood or serum sample is then stabilized. The tumor determination is obtained from a shift in the ratio of at least one of the IgG subclasses to the sum of the IgG subclasses, relative to the normal ratio in the samples.

11 Claims, 3 Drawing Sheets

IMMUNOLOGICAL METHOD FOR THE DETECTION OF MALIGNANT TUMORS AND KIT FOR PERFORMING THE METHOD

BACKGROUND OF THE INVENTION

Field of the Invention

The present invention pertains to a method of detecting malignant tumors and of determining their tumor mass through the characteristics of the serum-immune globuline G (IgG) of the patient.

It has been known for several years that in patients with malignant tumors one can detect a significant change in the amounts of the sulfhydryl or disulfide groups (measured by means of the dithionitrobenzoate reaction) within the serum-IgG. The experimental measurement value for the ratio of the sulhydryl to the disulfide groups is denoted the $\Sigma S$-value; whereby the reason for the change in the $\Sigma S$-value was unknown until recently.

In the course of further research in this area it has been shown that the change of the $\Sigma S$-value can be traced to a shift in the ratio of the subclass IgG1 relative to the other subclasses (e.g. IgG2).

This interrelation is new and, besides fundamental scientific knowledge, it offers the person of skill in the art a possibility of utilizing the phenomenon in diagnostics.

Independently thereof, research in this field has repeatedly shown that the measurement values in fresh blood or serum samples change relatively strongly within a short period of time. Performing the various analysis procedures for IgG on untreated blood or serum samples, therefore, does not render reproducible and plottable results.

SUMMARY OF THE INVENTION

It is therefore an object of the invention to provide results, reproducible during a sensible period of time of at least one day, with regard to the possible presence and the size and the development of a malignant tumor in a patient.

This is attained, in accordance with the invention, in that the fresh blood or serum samples of the patient are stabilized with radical inhibitors, preferably peroxide dimutase (SOD), and in that the shift is determined in the serum of the samples of the ratio of at least one of the IgG subclasses relative to the sum of the IgG subclasses as compared to the normal ratio.

Preferably, the shift of the ratio of the subclass IgG1 and/or the subcass IgG2 is determined in the serum of the stabilized samples relative to the sum of the IgG subclasses as compared to the normal ratio.

Examination performed on untreated samples with regard to the stability of the IgG1 values with the use of the radial immuno diffusion process (RID) according to Mancini exhibited a strong loss of the serum IgG1 level when the serum samples stand exposed to air. This effect ensues virtually immediately after blood withdrawal and it averages 20% after seven hours, at least 25% after 36 hours, whereby determinations are made with blood samples of healthy donors of both sexes.

The extent of the effect depends, among other things, on the level of the initial value: Samples with a high IgG1 value usually show a stronger reduction of the value, but it appears as though, according to preliminary results, other factors may be involved as well.

While the foregoing makes it already clear that an exact determination of the IgG1 level in the blood serum is not possible in the clinical environment without an effective stabilization, such stabilization becomes an absolute necessity when the shift in the ratio among the IgG subclasses is to be evaluated in the blood of cancer patients as a tumor marker in the spirit of the method according to the invention.

The stabilization with radical inhibitors appears to be very promising, but clearly the best results have so far been achieved with the addition of SOD. The SOD may be added to the fresh complete blood samples or to the serum samples after the blood cell material has been separated out.

Very advantageous stabilization results are attained when the stabilization of the serum with SOD is performed at a mass ratio of 100–1,000, preferably 300–400 iU SOD per ml serum.

It is thereby advantageous to add the SOD to the serum samples in solution with a concentration of 5,000–10,000 iU SOD/ml. The samples which are stabilized in this manner are subsequently tested with regard to the shift in the ratio of the subclass IgG1 relative to the sum of the IgG subclasses as compared with the normal ratio.

The change of the ratio of the IgG subclasses relative to one another in the bood serum could, very surprisingly, be tied to the appearance of malignant tumors and even to the number and the spreading of the tumor mass present in the body, so that it is possible to provide not only qualitative but also quantitative information about malignant tumors.

The method according to the invention is therefore preferably utilized in the external (extra-corporal) monitoring of tumor developments in a patient. Such a method is of great interest to the doctor in attendance primarily during or following a therapeutic treatment (monitoring). The method according to the invention can also be very successfully applied in preventive medicine, whereby a first indication towards a possible tumor development can be obtained in a simple manner.

The method does not at all inconvenience the patient and it is, according to experiences obtained so far, more dependable than other methods currently available. Of those, it is the tumor-marker process which is currently the one most often used.

In applying the method according to the invention in practical circumstances it became clear that the calculation of the above-noted ratio is advantageously based on heretofore known analytical methods for IgG, particularly chromatographic or immunological methods. The application of immuno-diffusion-assay has proven particularly successful in this context. Simple immuno-adsorptive column methods can be applied as well.

Furthermore, liquid adsorption chromatography was utilized as well, whereby extraordinary selectivity (separation discrimination) among the individual components can be attained. The resulting fractograms can be interpreted qualitatively and quantitatively.

Instead of the chromatographic methods, one may also wish to determine the $\Sigma S$-value as the measurement value, i.e. the value which is responsible for the sulfhydryl-disulfide ratio in the immune globuline G. Based on the recognition that this ratio is related with the ratio of subclasses $IgG_1$ to $IgG_2$. This measurement value is also a viable tool for performing the method according to the invention.

In the testing of the conditions for measuring the $\Sigma S$-value in the context of the method according to the invention, the observation was confirmed that malignant tumors can be distinguished from benign tumors with a high degree of accuracy.

With mammary carcinoma it was also possible to establish a correlation to the individual stages. A positive reaction of nearly 65% occured, for instance, in the $T_1$-stage, which climbed to 91% at $T_4$-stages. As compared with other tumor markers (e.g. CEA), this is a remarkable increase, as they possess a detection rate of about 5% in the $T_1$-stage. Reference is had, in this context, to the publication by M. Smola, W. Estelberger, M. Reiter, K. Schauenstein, and E. Schauenstein; in CANCER, Vol. 68, Nr. 5, 1991; page 1026.

The $\Sigma$S-value normalized after surgical operations. Depending on whether or not the operation was successful, the value remained normal or it again became pathological. M. Lahousen, E. Schauenstein, et al., Wiener Klin.Wschr.101, 858 (1989) [Vienna Clin.Weekly 101]. It is thus presumed that the $\Sigma$S-value is a measure for the humoral immune status, i.e. for the immune defense.

Another possibility of determining the ratio among the IgG subclasses exists in the method of radial immunodiffusion (RID).

It is common, however, with all of the methods that the results have merit only if the samples have been previously stabilized.

The formation of non-covalently bound aggregates, which cannot be detected with RID for instance, are presumed to be the reason for the instability of the IgG1 level. Previous results indicated that this aggregate formation is initiated by oxygen-containing radicals and, indeed, stabilization attempts with SOD proved to be especially successful.

DETAILED DESCRIPTION OF THE PREFERRED EMBODIMENTS AND EXAMPLES

Figure 1:
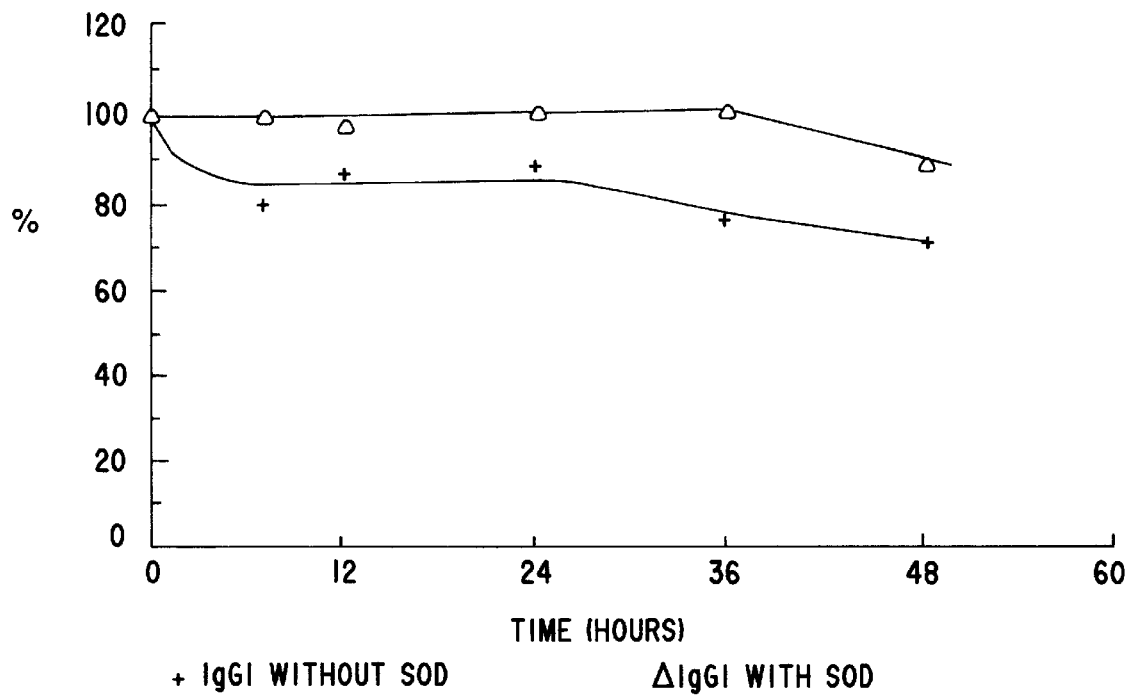
FIG. 1 is a plot diagram of IgG1 levels over time.

For performing these experiments, the serum was obtained from the complete blood of healthy donors by leaving the same standing until complete coagulation (clotting) and then centrifuge separation, and the serum was tested for IgG1 with or without SOD immediately or after 36 hours.

These tests were performed with RID in the first laboratory runs. It was shown that, with equal initial concentration of IgG1, the SOD-laced samples retained nearly the same concentration after 36 hours, while the non-stabilized samples sank to nearly half of the initial value.

Results in the separation of the IgG into its fractions by optimization experiments with protein-A-sepharose showed that it is principally possible by reducing the flow-through velocity to obtain degrees of purity of the immune globuline components of between 96 and 100%.

Based on these research results, the present invention also provides for a kit for performing the method according to the invention which is characterized with the stabilization reactant SOD and a system for determining the ratio of the subclass IgG1 to the other IgG subclasses.

The following examples are to serve in the explanation of the method according to the invention, without limiting the same in any way.

Example 1

Protocol of a Stabilization Experiment:

10 ml complete blood are drawn from the arm vein of a healthy donor. After 5 to 10 minutes coagulation is completed. Centrifuging is performed for 10 minutes at 440×g. The serum is pipetted off and separated into 4 aliquot portions of 0.1 ml each: Two zero time samples "0–" and "0+" and two samples for testing after 36 hours "36–" and "36+". The samples "0+" and "36+" are mixed with the appropriate amount of SOD (35 iU) (SOD lot 100H9311 of the firm Sigma through the firm Biotrade). The two zero samples are diluted with RID buffer 1:50 (0.05M tris, 0.10M NaCl; 1 g $NaN_3$/l; diluted HCl ad pH 8.0). The samples "36+" and "36–" are stored undiluted for 36 hours at room temperature in a closed condition at daylight. The samples "0–" and "0+" are immediately placed on the RID plate, whereby 3 $\mu$l per well are inserted. Agarose gel for the RID plates: 5 ml 1% agarose solution, 0.5 ml RID buffer, 0.5 anti-IgG1 serum (firm Binding Site, PE006). For dilutions of reference serum (firm Binding Site, PB062) are applied on the same plate: dilutions 1:10, 1:15, 1:25 and 1:50. The samples "36–" and "36+", after diluting with RID buffer 1:50, are also placed on the plate. Then the areas of the precipitate rings of "0–" and "0+" and of the diluted reference serum are measured, and two days later those of the 36 hour samples. Then the values of the areas of the precipitate rings measured for the dilutions of the reference serum are graphed against the known IgG1 concentrations of the dilutions. Finally, the surfaces of the precititate rings obtained from the four samples are graphed into the calibration diagram thus obtained, and the IgG1 concentrations are determined therefrom by interpolation.

TABLE 1

| Donor | Sample | | Sample | |
|---|---|---|---|---|
| | 0– | 0+ | 36– | 36+ |
| | IgG1 (mg/ml serum) | | | |
| G.R. | 10.24 | 10.00 | 6.59 | 9.76 |
| H.P | 8.91 | 8.99 | 5.72 | 8.89 |
| F.T. | 7.26 | 7.26 | 3.81 | 7.03 |

Example 2

In a 7-hour experiment similar to that in Example 1, the following results were obtained:

TABLE 2

| | IgG1 (mg/ml serum) | | | |
|---|---|---|---|---|
| | 0 h | 0 h + SOD | 7 h | 7 h + SOD |
| serum 1 | 6.77 | 6.97 | 6.38 | 6.97 |
| serum 2 | 5.45 | 5.45 | 4.55 | 5.45 |

All of the experiments performed so far have shown that the inhibiting effect of SOD under the conditions described is limited to between 36 and 40 hours, i.e. that the IgG determinations should in any case be performed during that time interval.

Example 3

Time lines were established with each serum sample (0.1 ml) in which the level of IgG1 and IgG2 was measured by means of RID without and after the addition of SOD (350 iU). The evaluation was effected in such a way that the measurement values obtained after different times were expressed in percent of the initial value. The result was a behavior over time for IgG1 and IgG2 as it is illustrated in the appended FIGS. 1 and 2, respectively.

Discussion of FIGS. 1 to 4 of the Appended Drawings

1. The decrease in the IgG1 level measurable with RID after a 48 hours waiting period (closed, aerobic, room temperature) averages 30%.

2. The effect apparently ensues immediately and reaches a decrease of about 20% after only 7 hours. The kinetic behavior points towards an exponential function and the experiments have shown that the relative temporal decrease of IgG1 is directly proportional to the respective reaction concentration of this subclass. Accordingly, kinetic behavior in accordance with the Michaelis/Menten function could be excluded and one could deduce that a reaction of the second order occurs here, most likely the primary formation of dimers, from which the higher aggregates then form. The formation of such aggregates would also explain that they are not detectable in RID, after it could be shown that heat aggregates do not form detectable precipitate rings in RID.

3. Whether the further reaction, between 12 and 24 hours, arrives at an intermediate self-stabilization of the system or it is a scattering of the measurement points, cannot be safely decided. It is only clear that the process subsequently runs continuously.

4. The inhibition of the reaction with SOD suggests that it likely is a self-aggregation induced by O-radicals. According to Wickens et al. (Biochim. Biophis. Acta, Vol.742:607–616, 1983), irradiation with small UV doses leads to self-aggregation and such aggregates—which, by the way, are induced by activated leucocytes—show a substantial reduction in the precipitate lines.

It follows from FIG. 1 that the IgG1 level averages a reduction of about 15% within 24 hours and of about 22% within 36 hours. Within this time span, the decrease can be inhibited virtually completely with the addition of SOD. The importance of this result becomes evident if one considers that in FIG. 1 the mean percentual decreases are graphed and that the individual decreases measured with the separate samples can in certain cases be substantially greater, as illustrated in the following table 3.

TABLE 3

| IgG1 | IgG1 + SOD | IgG1 | IgG1 + SOD | IgG1 | IgG1 + SOD | IgG1 | IgG1 + SOD |
|---|---|---|---|---|---|---|---|
| 0 h | | 24 h | | 36 h | | 48 h | |
| (mg/ml serum) | | | | | | | |
| 12.16 | 12.67 | 9.73 | 10.67 | — | — | 7.46 | 9.02 |
| 8.91 | 8.49 | 6.98 | 8.11 | 5.72 | 8.89 | 5.37 | 9.48 |
| 10.09 | 9.71 | 8.69 | 10.09 | 5.72 | 9.48 | 5.04 | 6.45 |
| 10.71 | 9.89 | 11.13 | 10.92 | 6.97 | 9.92 | 4.87 | 9.28 |
| 8.43 | 9.41 | 7.72 | 8.69 | 6.35 | 8.69 | 5.05 | 5.26 |
| 7.26 | 7.26 | 4.41 | 7.96 | 3.81 | 7.03 | 2.28 | 6.35 |

Example 4

In this example, 16 serum samples of healthy donors were tested. First, the level of IgG1 and IgG2 was measured by means of RID. The values thus obtained are listed in the following table 4.

TABLE 4

| | IgG1 | IgG1 with SOD | IgG2 | IgG2 with SOD |
|---|---|---|---|---|
| | | (mg/ml serum) | | |
| | 6.77 | 6.97 | 3.13 | 3.29 |
| | 5.45 | 5.45 | 2.64 | 2.79 |
| | 8.57 | 8.57 | 3.34 | 3.20 |
| | 8.34 | 8.80 | 1.67 | 1.55 |
| | 8.12 | 8.35 | 3.20 | 2.94 |
| | 12.16 | 12.67 | 4.18 | 4.33 |
| | 9.03 | 8.34 | 2.94 | 2.80 |
| | 6.83 | 6.83 | 2.63 | 2.79 |
| | 11.15 | 11.39 | 3.56 | 3.73 |
| | 9.95 | 9.48 | 4.38 | 5.42 |
| | 13.41 | 12.90 | 2.33 | 2.04 |
| | 8.91 | 8.49 | 3.60 | 3.59 |
| | 10.09 | 9.71 | 3.77 | 3.60 |
| | 10.71 | 9.89 | 6.56 | 6.97 |
| | 8.43 | 9.41 | 3.55 | 3.85 |
| | 7.26 | 7.26 | 1.48 | 1.72 |
| Avg. | 9.07 | 9.03 | 3.31 | 3.41 |
| SEM. | 0.52 | 0.51 | 0.29 | 0.34 |

Additionally, we could refer back to six further values, which are listed in table 5.

TABLE 5

| | IgG1 | IgG2 |
|---|---|---|
| | mg/ml serum | |
| | 6.79 | 3.04 |
| | 7.09 | 2.45 |
| | 5.86 | 1.43 |
| | 6.82 | 1.61 |
| | 5.76 | 2.79 |
| | 5.75 | 2.65 |
| Avg. | 6.35 | 2.33 |
| SEM: | 0.25 | 0.27 |

When the mean values thus obtained are averaged, the results for the 22 healthy donor serums are 8.33±0.48 mg IgG1 and 3.04±0.25 mg IgG2/ml serum.

Figure 2:
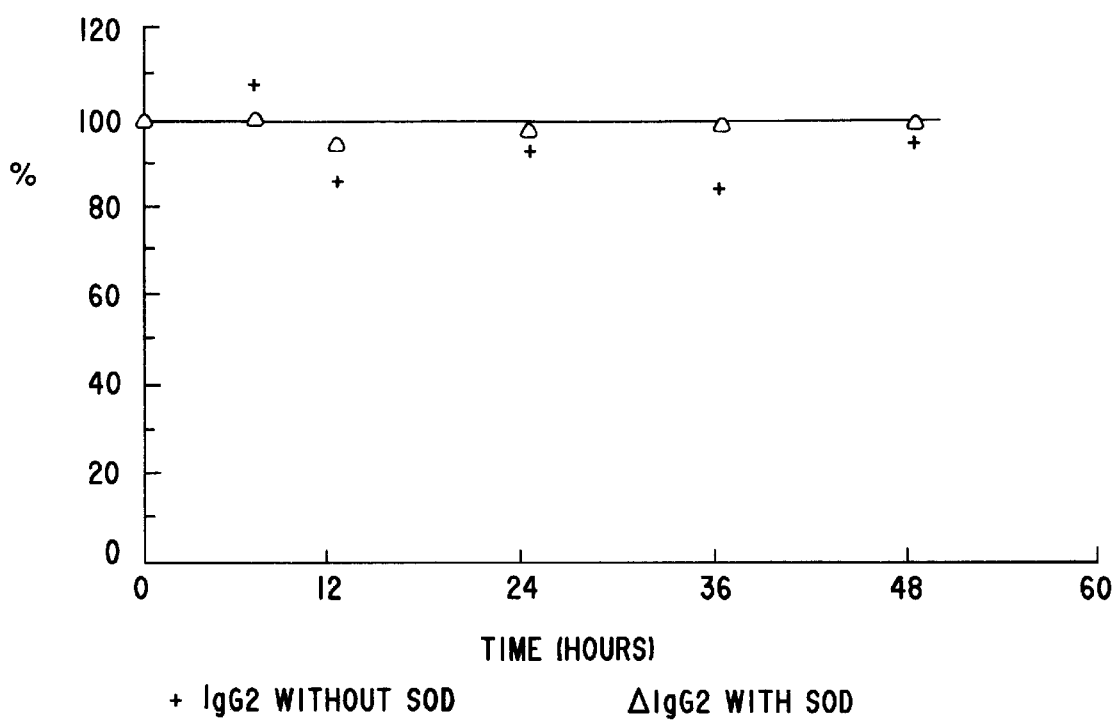
FIG. 2 is a similar diagram of IgG2 levels.
Figure 3:
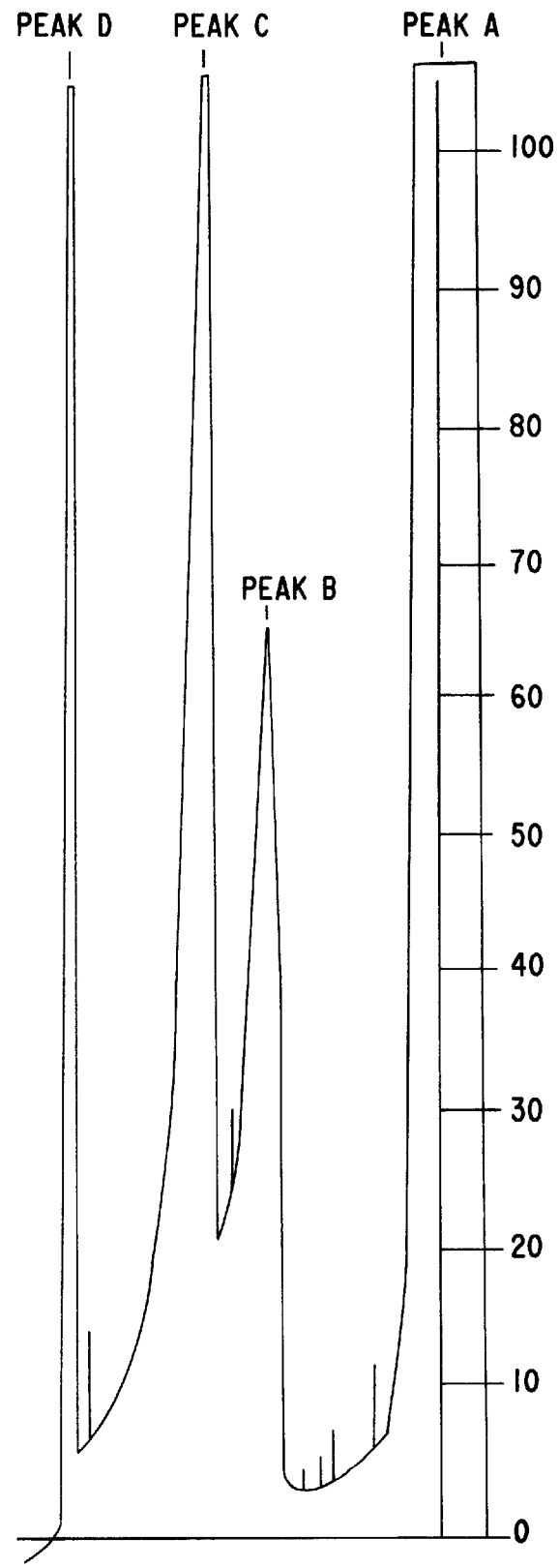
FIG. 3 is a fractogram.
Figure 4:
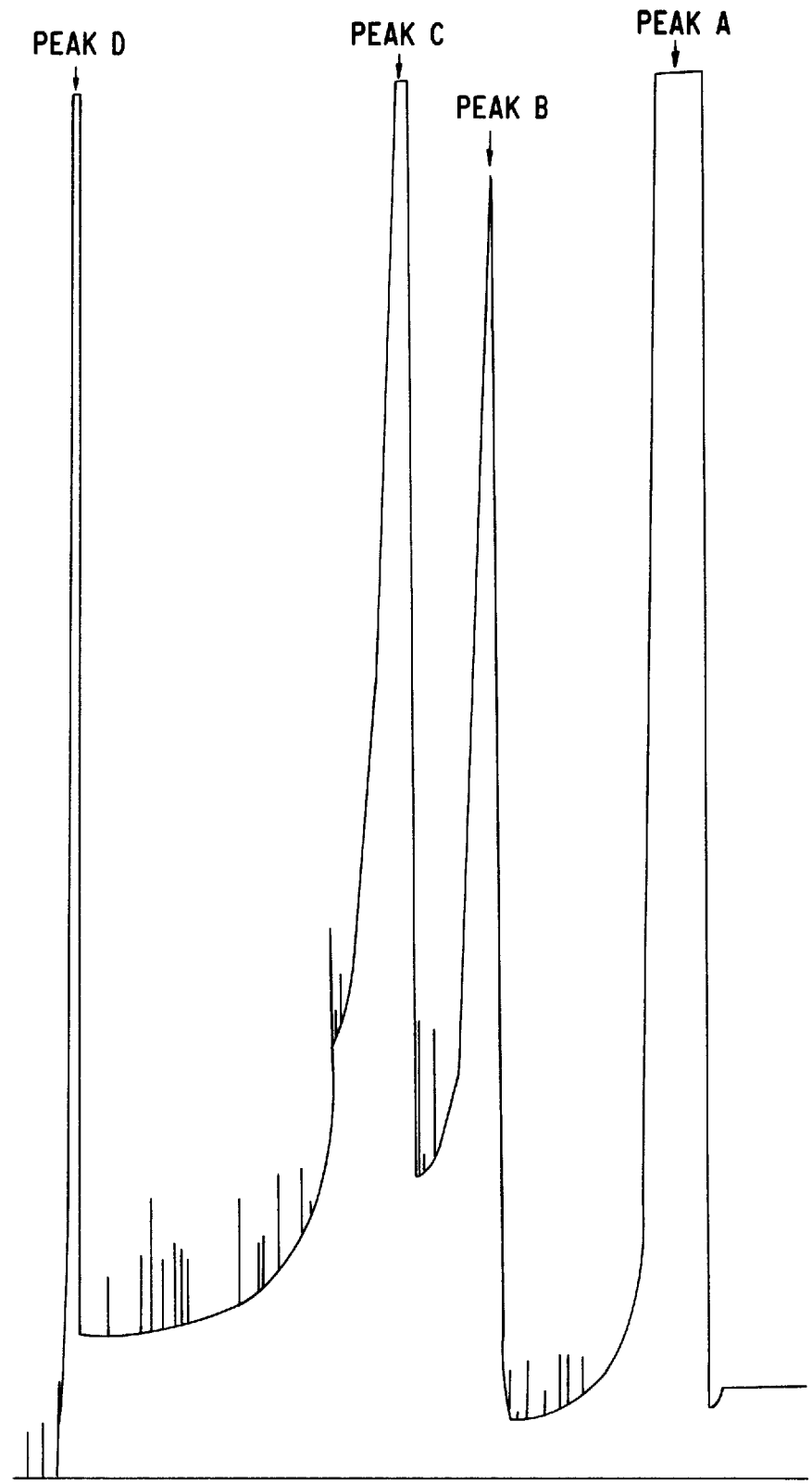
FIG. 4 is a similar fractogram.

The IgG1 levels in cancer serums average 23 to 24% lower than normal serums, so that the absolute necessity of an efficient inhibition is evident. SOD fulfills this requirement, however only up to a shelf time of the serum of about 40 hours, which, however, should suffice in most cases. It is quite remarkable that a clearly defined time effect, as it is illustrated in FIG. 1, occurs only for IgG1, while IgG2, the second main component, shows irregular fluctuations, which, however, are inhibited as well with SOD (FIG. 2). Since SOD inhibits the decrease of IgG1 indicated in the RID and since only this subclass contains a reactive disulfide bridge SS* in the molecule, it becomes clear that SOD can also be utilized as a stabilizer for the measurement of the ΣS-value, which consists of the term for SS* to 85%.

Example 5

Separation of the IgG subclasses 1 and 2 at protein-A-sepharose columns.

Buffer Composition:

0.05M phosphate-citrate buffer pH 4.7

0.086M phosphate-citrate buffer pH 4.3

Flow speeds vary between 70 ml/h and 10 ml/h.

The appended fractograms (FIGS. 3 and 4) were obtained in which at the relevant peaks B and C degrees of purity were achieved for the components of up to 96% and 100%, respectively.

Example 6
Determination of the IgG1 and IgG2 Concentrations on the One Hand with Affinity-Chromatography with Protein-A-Sepharose and, on the Other Hand, with RID for Reference For the purpose of comparing the two methods, serums of 20 healthy donors and serums of 40 female patients with ovarial, cervical, and colon carcinomas were used, whereby the blood samples were taken prior to operation.

The blood samples (2–10 ml) were centrifuged immediately after having been taken at 440×g for 10 minutes, the serum was pipetted off, diluted at 1:50 with RID buffer, and applied to the RID plates. The precipitate rings were measured after 2 days and the IgG1 and IgG2 concentrations were determined with a reference serum (Mancini technique).

0.3 ml serum was applied on the column (K 9/15) for isolation of IgG1 and IgG2 by means of protein-A-sepharose, and eluted with 0.16M phosphate-citrate buffer pH 7.0 and a flow velocity of 10 ml/h. The IgG thereby binds via the Fc portion to the protein-A and the other serum proteins are eluted in an unbound state. Besides IgG, IgM and IgA are also bound to protein-A. After the baseline is reached, a buffer exchange is effected: first, IgG2 is eluted with 0.05 M phosphate-citrate buffer pH 4.7 and then IgG1 with 0.086M phosphate-citrate buffer pH 4.3. Then the gel is cleaned with 0.1M citrate buffer and then the citrate buffer is exchanged for the starting buffer (0.16M phosphate-citrate buffer pH 7.0). The eluates of IgG1 and IgG2 are titrated with 1N NaOH to pH 7.0 and the protein concentration is photometrically determined at 278 nm. The extinction coefficient $\epsilon'=1.58$ then allows the determination of the concentration.

Table 6 lists the mean values of the IgG1 and IgG2 concentrations of the serum samples (±sem), determined with RID and with protein-A. The quotient G1/G2 can then be determined from these two values.

TABLE 6a

| | determined with RID | | | |
|---|---|---|---|---|
| | IgG1 | IgG2 | G1/G2 | n |
| | (mg/ml serum) | | | |
| Healthy samples | 8.72 ± 0.41 | 3.66 ± 0.31 | 2.62 ± 0.21 | 20 |
| Gyn. tumors | 6.70 ± 0.50 | 3.69 ± 0.35 | 2.04 ± 0.14 | 40 |

TABLE 6b

| determined with protein-A | | | |
|---|---|---|---|
| IgG1 | IgG2 | G1/G2 | n |
| (mg/ml serum) | | | |
| 7.27 ± 0.36 | 3.14 ± 0.25 | 2.54 ± 0.22 | 20 |
| 5.75 ± 0.37 | 3.16 ± 0.29 | 2.08 ± 0.13 | 40 |

Determined with RID, the mean values of the IgG1 concentrations between healthy donors and tumor patients differ highly significantly (p=0.005), whereby 27.5% incorrect negative and 25% incorrect positive results were obtained. The isolation of IgG1 with protein-A shows a similar result: p=0.005 and 30% incorrect negative and 35% incorrect positive results.

We claim:

1. A method of screening for malignant tumors, which comprises:
   withdrawing blood from a patient, and preparing samples of blood or serum obtained therefrom;
   stabilizing the blood or serum sample with a radical inhibitor;
   determining (i) the amount of at least one immune globulin G subclass and (ii) the amount of all immune globulin G subclasses in the sample;
   calculating the ratio between (i) and (ii) and comparing the ratio with the ratio of (i) and (ii) in a normal serum or blood sample;
   wherein a shift of the ratio of (i) and (ii) relative to the ratio in a normal sample is indicative of the presence of a tumor in the patient.

2. The method according to claim 1, which further comprises selecting peroxide dismutase (SOD) as the radical inhibitor in the stabilizing step.

3. The method according to claim 2, wherein the stabilizing step comprises stabilizing the serum with SOD in a mass ratio of 100 to 1000 iU SOD per ml serum.

4. The method according to claim 2, wherein the stabilizing step comprises stabilizing the serum with SOD in a mass ratio of 300 to 400 iU SOD per ml serum.

5. The method according to claim 1, which further comprises:
   determining (i) the amount of at least one of the immune globulin subclasses IgG1 and IgG2 and (ii) the amount of all immune globulin G subclasses in the sample;
   calculating the ratio between (i) and (ii) and comparing the ratio with the ratio of (i) and (ii) in a normal serum or blood sample;
   wherein a shift of the ratio of (i) and (ii) relative to the ratio in a normal sample is indicative of the presence of a tumor in the patient.

6. The method according to claim 1, wherein the determining step comprises determining the shift of the ratio by ascertaining a $\Sigma S$-value.

7. The method according to claim 1, wherein the calculating step comprises calculating the shift of the ratio from results obtained from a chromatographic method.

8. The method according to claim 1, wherein the calculating step comprises calculating the shift of the ratio from results obtained from an immunological method.

9. The method according to claim 1, wherein the calculating step comprises calculating the shift of the ration via an immuno-diffusion assay.

10. A kit for screening for malignant tumors, wherein the tumor is detected by withdrawing blood from a patient, preparing blood or serum samples, stabilizing the blood or serum sample with a radical inhibitor, determining (i) the amount of at least one of the immune globulin G subclasses and (ii) the amount of all immune globulin G subclasses in the sample, calculating the ratio between (i) and (ii) and comparing the ratio with the ratio of (i) and (ii) in a normal serum or blood sample; wherein a shift of the ratio of (i) and (ii) relative to the ratio in a normal sample is indicative of the presence of a tumor in the patient, and wherein the kit comprises:
   A stabilizing reagent for inhibiting radical formation in the blood or serum sample, and
   means for determining the amount of at least one immune globulin G subclass in the serum and means for determining the amount of all immune globulin G subclasses.

11. The kit according to claim 10, wherein said stabilizing reagent is peroxide dismutase.

* * * * *

UNITED STATES PATENT AND TRADEMARK OFFICE
CERTIFICATE OF CORRECTION

PATENT NO. : 5,837,474
DATED : November 17, 1998
INVENTOR(S) : Erwin Schauenstein et al.

It is certified that error appears in the above-identified patent and that said Letters Patent is hereby corrected as shown below:

On the title page,
Item [30] should read as follows:

Feb. 27, 1992   [AT]    Austria ............ 368/92

Signed and Sealed this

Eighteenth Day of May, 1999

Attest:

Q. TODD DICKINSON

Attesting Officer

Acting Commissioner of Patents and Trademarks